(12) United States Patent
Francke

(10) Patent No.: US 7,127,029 B2
(45) Date of Patent: Oct. 24, 2006

(54) ARRANGEMENT AND METHOD FOR OBTAINING TOMOSYNTHESIS DATA

(75) Inventor: Tom Francke, Sollentuna (SE)

(73) Assignee: XCounter AB, Danderyd (SE)

( * ) Notice: Subject to any disclaimer, the term of this patent is extended or adjusted under 35 U.S.C. 154(b) by 151 days.

(21) Appl. No.: 10/849,209

(22) Filed: May 20, 2004

(65) Prior Publication Data

US 2005/0226367 A1    Oct. 13, 2005

(30) Foreign Application Priority Data

Mar. 30, 2004  (SE)  .................................... 0400822

(51) Int. Cl.
*G01N 23/083* (2006.01)
(52) U.S. Cl. .................. 378/22; 378/25; 378/196; 378/197
(58) Field of Classification Search .............. 378/9, 378/13, 25, 196, 2, 22; 250/363, 363.02, 250/382, 389, 363.05, 454.11
See application file for complete search history.

(56) References Cited

U.S. PATENT DOCUMENTS

| | | | | |
|---|---|---|---|---|
| 4,084,094 | A | * | 4/1978 | Froggatt ........................ 378/10 |
| 4,101,774 | A | * | 7/1978 | Elzinga et al. ................ 378/25 |
| 4,349,740 | A | * | 9/1982 | Grassmann et al. .......... 378/25 |
| 4,357,708 | A | * | 11/1982 | Baeker ......................... 378/25 |
| 4,566,112 | A | * | 1/1986 | Linde et al. .................... 378/2 |
| 4,665,540 | A | * | 5/1987 | Kunert ......................... 378/21 |
| 5,060,246 | A | * | 10/1991 | Van Der Brug et al. ...... 378/20 |
| 5,331,553 | A | * | 7/1994 | Muehllehner et al. . 250/363.02 |
| 6,118,125 | A | | 9/2000 | Carlson et al. |
| 6,236,709 | B1 | * | 5/2001 | Perry et al. ................... 378/57 |
| 6,242,743 | B1 | | 6/2001 | DeVito et al. |
| 6,303,935 | B1 | * | 10/2001 | Engdahl et al. ........ 250/363.03 |
| 6,320,929 | B1 | | 11/2001 | Von Der Haar |
| 6,337,482 | B1 | | 1/2002 | Francke |
| 6,365,902 | B1 | * | 4/2002 | Francke et al. ............. 250/382 |

(Continued)

FOREIGN PATENT DOCUMENTS

CA    2277251  A1 *  1/2001

OTHER PUBLICATIONS

International Search Report dated Jun. 15, 2005 for International Application No. PCT/SE2005/000386.

(Continued)

*Primary Examiner*—Edward J. Glick
*Assistant Examiner*—Anastasia S. Midkiff
(74) *Attorney, Agent, or Firm*—Harness, Dickey & Pierce

(57) ABSTRACT

A scanning-based arrangement for obtaining tomosynthesis data of an object (5) at high repetition rate comprises a support structure (11); scanning-based apparatuses (10) fixedly arranged on the support structure and each including (i) radiation source (1), and (ii) a radiation detector (6) comprising a stack of line detectors (6a), each being directed towards the radiation source to allow a ray bundle ($b_1, \ldots, b_n, \ldots, b_N$) of radiation that propagates in a respective one of various different angles ($\alpha_1, \ldots, \alpha_n, \ldots, \alpha_N$) to enter the line detector; an object table (13) arranged in the radiation path of one of the scanning-based apparatuses; and a device (14) provided for rotating the support structure relative the object table so that the object table will successively be arranged in the radiation path of each of the scanning-based apparatuses, during which rotation each of the line detectors of each of the scanning-based apparatuses is adapted to record a plurality of line images of radiation as transmitted through the object.

39 Claims, 4 Drawing Sheets

U.S. PATENT DOCUMENTS

| | | | |
|---|---|---|---|
| 6,373,065 B1 * | 4/2002 | Francke et al. | 250/374 |
| 6,385,282 B1 | 5/2002 | Francke | |
| 6,414,317 B1 | 7/2002 | Francke | |
| 6,476,397 B1 | 11/2002 | Francke | |
| 6,477,223 B1 | 11/2002 | Francke | |
| 6,501,822 B1 * | 12/2002 | Roder | 378/22 |
| 6,518,578 B1 | 2/2003 | Francke | |
| 6,522,722 B1 | 2/2003 | Francke | |
| 6,546,070 B1 | 4/2003 | Francke | |
| 6,570,954 B1 * | 5/2003 | Rasche et al. | 378/21 |
| 6,760,399 B1 * | 7/2004 | Malamud | 378/9 |
| 6,970,531 B1 * | 11/2005 | Eberhard et al. | 378/26 |
| 2003/0155519 A1 | 8/2003 | Francke et al. | |

OTHER PUBLICATIONS

International-Type Search Report dated Oct. 29, 2004 for International-type search request No. SE 04/00182.

* cited by examiner

ARRANGEMENT AND METHOD FOR OBTAINING TOMOSYNTHESIS DATA

FIELD OF THE INVENTION

The invention relates generally to scanning-based arrangements and methods for obtaining tomosynthesis data at high repetition rates for time-resolved examination of an object.

BACKGROUND OF THE INVENTION AND RELATED ART

An X-ray medical diagnostic method such as mammography is a low-dose procedure that creates one or more images of a part of a patient such as a breast thereof, which is to be examined, e.g. for detection of early stages of cancer.

The mammography diagnostic procedure generally includes obtaining two images of each of the patient's breasts, one from above and one from the side. A physician or radiologist then reviews the images of the breast, i.e., mammograms, to identify any breast cancer.

While this procedure is one of the best methods of detecting early forms of breast cancer, it is still possible for the detection of breast cancer to be missed by a physician or radiologist reviewing the mammograms. For example, breast cancer may be missed by being obscured by radiographically dense, fibroglandular breast tissue.

Tomosynthesis imaging, in which a plurality of images is acquired at different angles, has been studied in an effort to detect early forms of breast cancer. By combining the plurality of images, it is possible to reconstruct any plane in the breast being imaged that is parallel to the detector. The higher number of images is utilized, the better image quality in the reconstructed tomosynthesis images is obtained.

Further, various line detectors for detecting ionizing radiation are known in the art. While such detectors provide for instantaneous one-dimensional imaging, two-dimensional imaging can only be performed by means of scanning the line detector, and optionally the radiation source, in a direction traverse to the one-dimensional detector array. To use such a detector in tomosynthesis, wherein a plurality of images has to be acquired at different angles would be very time consuming.

SUMMARY OF THE INVENTION

A main aim of the invention is therefore to provide a scanning-based arrangement and a method, respectively, for obtaining tomosynthesis data of an object at a higher speed than what is obtainable by using scanning-based apparatuses and methods of the prior art.

In this respect there is a particular aim to provide such an arrangement and such a method, which are capable of collecting, by means of scanning-based detection, tomosynthesis data in order to reconstruct three-dimensional images of the object at high repetition rate.

A further aim of the invention is to provide such an arrangement and such a method, which is operable, while exposing the object for a low radiation dose.

A still further aim of the invention is to provide such an arrangement and such a method, which are uncomplicated and can produce high-quality two-dimensional tomosynthesis images with high spatial resolution, high sensitivity, high signal-to-noise ratio, high dynamic range, high image contrast, and low noise from overlaying tissue.

A yet further aim of the invention is to provide such an arrangement and such a method, which are reliable, accurate, and inexpensive.

A still further aim of the invention is to provide such an arrangement and such a method, which do not need the use of a complete computerized tomography (CT) apparatus.

These objects, among others, are attained by arrangements and methods as claimed in the appended claims.

According to one aspect of the present invention

The data from the apparatus is excellent to be used in tomosynthesis or laminographic imaging.

The line detectors uses are preferably, but not exclusively, gaseous-based parallel plate detectors. Other line detectors that may be used include scintillator-based arrays, CCD arrays, TFT- and CMOS-based detectors, liquid detectors, and diode arrays, e.g. PIN-diode arrays with edge-on, near edge-on or perpendicular incidence of X-rays.

Further characteristics of the invention and advantages thereof, will be evident from the detailed description of preferred embodiments of the present invention given hereinafter and the accompanying FIGS. 1–4, which are given by way of illustration only, and thus, are not limitative of the present invention.

DESCRIPTION OF PREFERRED EMBODIMENTS

Figure 1:
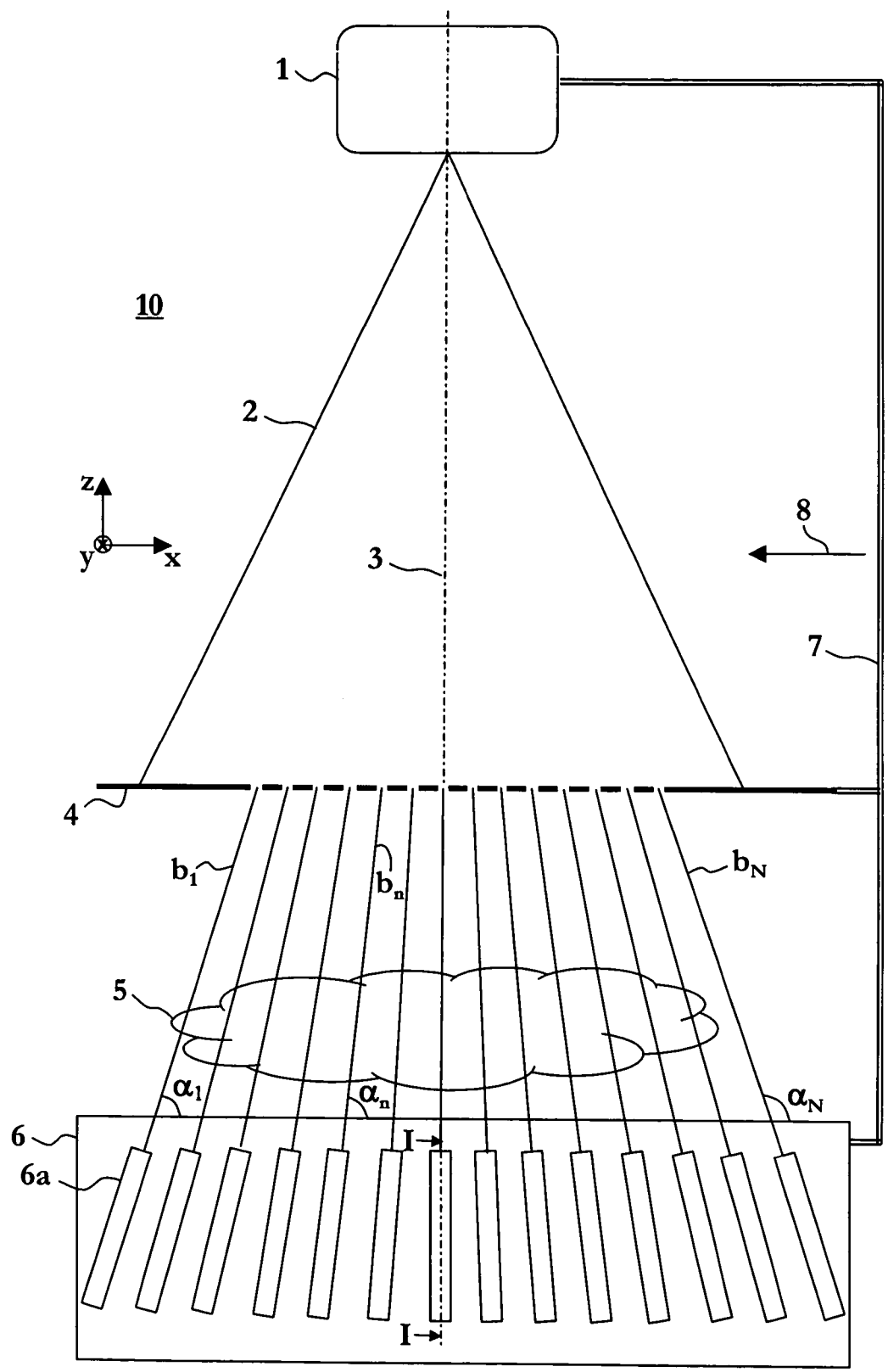
FIG. 1 illustrates schematically, in a side view, an apparatus for obtaining tomosynthesis data for x-ray examination of an object.

An apparatus 10 for obtaining tomosynthesis data for x-ray examination of an object 5 is shown in FIG. 1. The apparatus 10 comprises a divergent X-ray source 1, which produces X-rays 2 centered around an axis of symmetry 3, which is parallel with the z axis, a collimator 4, a radiation detector 6, and a structure 7 for rigidly connecting the X-ray source 1, the collimator 4, and the radiation detector 6 to each other.

The radiation detector 6 comprises a stack of line detectors 6a, each being directed towards the divergent radiation source 1 to allow a respective ray bundle $b_1, \ldots, b_n, \ldots, b_N$ of the radiation 2 that propagates in a respective one of a plurality of different angles $\alpha_1, \ldots, \alpha_n, \ldots, \alpha_N$ with respect to the front surface of the radiation detector 6 to enter the respective line detector 6a.

The collimator 4 may be a thin foil of e.g. tungsten with narrow radiation transparent slits cut or etched away, the number of which corresponds to the number of line detectors 6a of the radiation detector 6. The slits are aligned with the line detectors 6a so that X-rays passing through the slits of the collimator 4 will reach the detector units 6a, i.e. as the respective ray bundles $b_1, \ldots, b_n, \ldots, b_N$. The collimator 4, which is optional, prevents radiation, which is not directed directly towards the line detectors 6a, from impinging on the object 5 to be examined, thereby reducing the radiation dose to the object. This is advantageous in all applications where the object is a human or an animal, or parts thereof.

In U.S. patent application Ser. No. 10/657,241 is disclosed to use such a detector apparatus for linear scanning of the object 5 to obtain tomosynthesis data thereof in order to reconstruct two-dimensional and even three-dimensional images of the object 5. The contents of the above U.S. patent application are hereby incorporated by reference.

During such scanning the device 7 moves the radiation source 1, the collimator 4, and the radiation detector 6 relative the object 5 in a linear manner parallel with the front of the radiation detector as being indicated by arrow 8, while each of the line detectors 6a records a plurality of line images of radiation as transmitted through the object 5 in a respective one of the different angles $\alpha_1, \ldots, \alpha_n, \ldots, \alpha_N$. The scanning of the object 5 is preferably performed a length, which is sufficiently large so that each one of the line detectors 6a can be scanned across the entire object of interest to obtain, for each of the line detectors 6a, a two-dimensional image of radiation as transmitted through the object 5 in a respective one of the different angles $\alpha_1, \ldots, \alpha_n, \ldots, \alpha_N$.

Figure 2A:
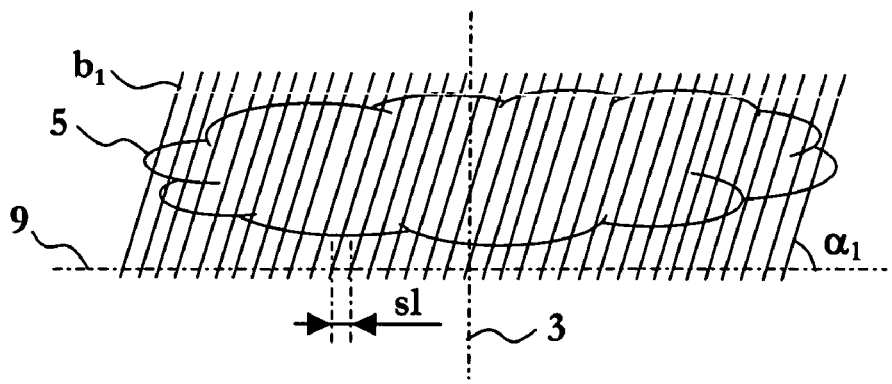
FIGS. 2a–c illustrate each schematically, in a side view, a particular X-ray bundle as it traverses the examination object during scanning by the apparatus of FIG. 1.
Figure 2B:
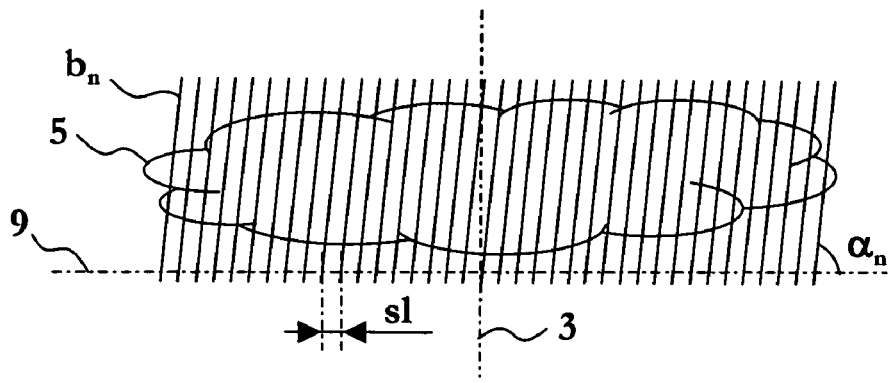
Figure 2C:
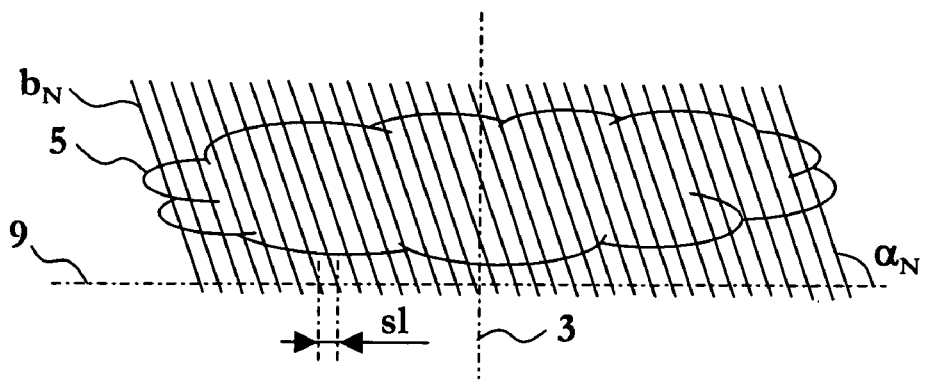

In FIGS. 2a–c three different X-ray bundles $b_1$, $b_n$, and $b_N$ are schematically illustrated as they traverse the examination object 5 during scanning by the apparatus of FIG. 1. Reference numeral 9 indicates a plane parallel with the x axis, which coincides with the scanning direction 8 and with the front of the radiation detector 2.

As can be seen in FIGS. 2a–c each line detector/X-ray bundle pair produces a complete two-dimensional image at a distinct one of the different angles. FIG. 2a illustrates the formation of a two-dimensional image of radiation transmitted through the object at an angle $\alpha_1$, FIG. 2b illustrates the formation of a two-dimensional image of radiation transmitted through the same object, but at an angle $\alpha_n$, and FIG. 2c illustrates the formation of a similar two-dimensional image, but at an angle $\alpha_N$.

While such a detector scanning technique provides for the recording of tomosynthesis data of the object, i.e. the simultaneous recording of a number of two-dimensional X-ray transmission images at high speed, it is not suitable to record several images one after each other to observe time dependent examination, such as e.g. positioning of catheters, and to visualize matter in motion, such as e.g. heart, blood, contrast agents, etc., since the scanning movement has to be retarded, stopped, and accelerated in the opposite direction in order to perform a second scan of the object. Such actions are time-consuming and suffer from stability and alignment problems due to the strong forces the detectors experience during the retardations and accelerations.

Further, to obtain a large angular spread of the tomosynthesis data, i.e. a large opening angle of the radiation irradiating the detector apparatus, the detector apparatus has to be long in the scanning direction, which gives a long scanning distance. The scanning speed has therefore to be high, which puts higher demands on the retardation and acceleration of the detector apparatus at the start and end of the scanning movement.

In computerized tomography (CT) there is a trend today to record more and more images per second by increasing the rotational speed, and to use more and more detector rows, e.g. 4, 8 and even 16 rows, in a CT line detector to obtain time-resolved measurements. Lately, discussions with use 64 and up to 256 rows of detectors have been made. The costs for the detector increase to unreasonable high levels for detectors having such many detector rows.

When the number of images per second increases the radiation dose to the patient, which is high enough already, will increase further. One goal of CT today is to be capable of recording time-resolved three-dimensional images of e.g. a heart.

In order to be capable of performing time-resolved tomosynthesis measurements with high repetition rate using the scanning-based technique described above several modifications have to be made.

Figure 3:
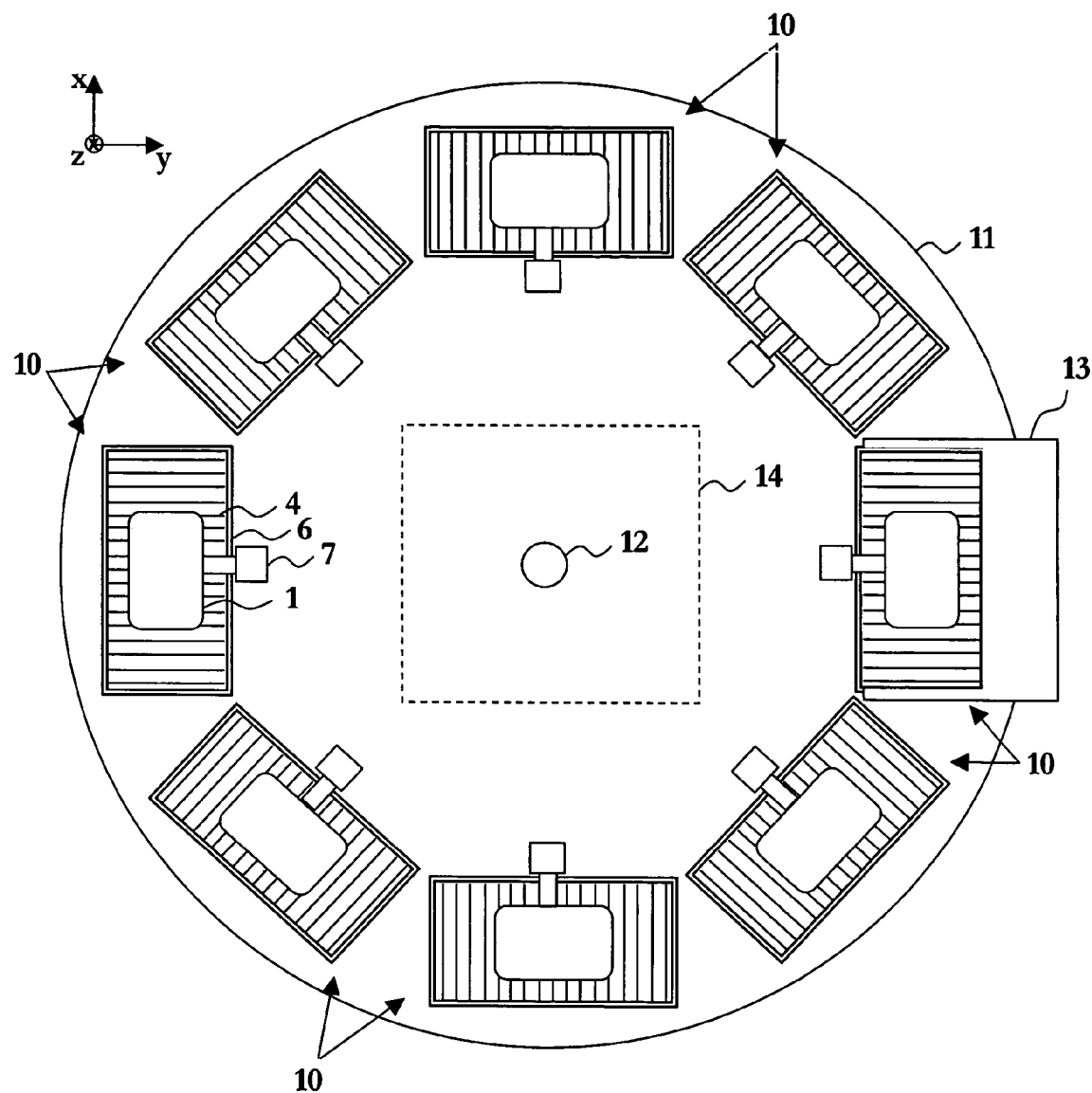
FIG. 3–4 illustrate each schematically, in a top view, an arrangement for obtaining tomosynthesis data at a high repetition rate for x-ray examination of an object according to a preferred embodiment of the present invention, the arrangement comprising a plurality of the apparatus of FIG. 1.

An arrangement for obtaining tomosynthesis data at high repetition rates for x-ray examination of an object according to a preferred embodiment of the present invention is schematically illustrated in FIG. 3 in top view. The arrangement comprises a plurality of the apparatus 10 of FIG. 1 arranged on a support structure 11 having an axis 12 of rotation. The apparatuses 10 are arranged on the support structure 11, which preferably consists of an essentially circular disk or plate, at essentially similar distances from the axis 12 of rotation, and preferably equiangularly around the axis 12 of rotation, i.e. adjacent ones of the apparatuses 10 are arranged with an essentially constant distance between them. The apparatuses 10 are standing on the support structure 11 so that the axis of symmetry 3 of the radiation 2, which is parallel with the z axis, is parallel with the normal of the support structure 11, which extends in the xy plane. The X-ray source 1, the collimator 4, the radiation detector 6, and the rigidly connecting structure 7 are clearly visible in FIG. 3.

Further, an object table 13 on which the object to be examined is provided. The object table 13 is initially arranged in the radiation path between the collimator 4 and the radiation detector 6 of one of the scanning-based apparatuses. Note that the object table is not supported by the support structure 11, but by another support structure (not illustrated).

A device 14 is provided for rotating the support structure 11 around the axis 12 of rotation relative the object table 13 so that the object table 13 will successively be arranged in the radiation path between the divergent radiation source and the radiation detector of each of the scanning-based apparatuses 10 of the arrangement. During the rotation each of the line detectors 6a of each of the scanning-based apparatuses 10 is adapted to record a plurality of line images of radiation as transmitted through the object in a respective one of different angles.

Note that the detector apparatuses 10 are active in consecutive order. The X-ray radiation source 1 has thus only to be switched on during the time it is aligned with the object table 13 and thus has to produce radiation for the measurement.

Preferably, the device provided for rotating is adapted to rotate the support structure 11 relative the object table 13 at least an angle, e.g. one full revolution, which is sufficient for scanning each of the line detectors 6a of each of the scanning-based apparatuses 10 across the entire object to obtain, for each of the line detectors 6a of each of the scanning-based apparatuses 10, a two-dimensional image of radiation.

By means of the arrangement several sets of two-dimensional images for tomosynthesis reconstruction can be recorded after each other without having to retard, stop and accelerate the detectors. They preferably are simply rotated at a constant rotational speed.

Note that a difference in the scanning movement for each detector apparatus 10 is obtained relative the scanning disclosed in the U.S. patent application Ser. No. 10/657,241. In this application a linear scanning in the x direction is described, whereas in the present invention the scanning direction is along the periphery of a circle arranged in the xy plane. However, the larger the radius of the circle is, the more similar to a linear movement is obtained.

The distance between the detector apparatuses 10 and the axis 12 of rotation is preferably between about 0.5 m and about 4 m, more preferably between about 0.5 m and about 2 m, and most preferably about 1 m.

The more detector apparatuses that are arranged on the support structure 11, the higher repetition rate in the time-resolved tomosynthesis recording is obtained for a given rotational speed of the support structure 11.

The number of the scanning-based apparatuses 10 is preferably between 2 and 20, more preferably between 2 and 10, and most preferably between 4 and 8. A typical figure would be 5.

The device 14 provided for rotating is adapted to rotate said support structure 11 relative the object table 13 at a rotational speed of preferably between about 0.2 revolutions per second and about 10 revolutions per second, more preferably between about 0.5 revolutions per second and about 5 revolutions per second, and most preferably between about 0.5 revolutions per second and about 2 revolutions per second. A typical figure would be one full revolution per second.

This gives a repetition rate of between about 0.4 images/second and about 200 images per second. The typical figures given above correspond to a repetition rate of about 5 images per second.

The different angles $\alpha_1, \ldots, \alpha_n, \ldots, \alpha_N$ are distributed over an angular range $\alpha_N-\alpha_1$ of preferably at least 5°, more preferably at least 20°, and most preferably at least 45° depending on the application or kind of examination in order to obtain high-quality tomosynthesis data for examination of the object. A typical value is 90°.

The length in the radial direction of each of the line detectors 6a in the stack of line detectors of each of the scanning-based apparatuses 10 is preferably between about 0.05 m and 2 m, more preferably between about 0.1 m and 1 m, and most preferably between about 0.2 m and 0.5 m. Similarly, the stack of line detectors of each of the scanning-based apparatuses 10 is preferably in the tangential direction between about 0.2 m and 2 m, more preferably between about 0.4 m and 1.5 m, and most preferably between about 0.75 m and 1.25 m. The sizes of the detector apparatuses 10 depend on the particular application the arrangement is to be used for.

The number of line detectors 6a in the stack of line detectors of each of the scanning-based apparatuses 10 is at least 2, preferably at least 5, more preferably at least 10, and most preferably between about 20 and about 50, depending on the number of images recorded at different angles, which is required during the examination. It can be as high as several hundred line detectors 6a.

The scanning step, in FIGS. 2a–c denoted by s1, depends on the spatial resolution of the two-dimensional images formed from the one-dimensional recordings. Typically, the scanning step s1 can be about 10–500 microns, and the individual detecting elements of each of the line detectors can be of similar size.

Figure 4:
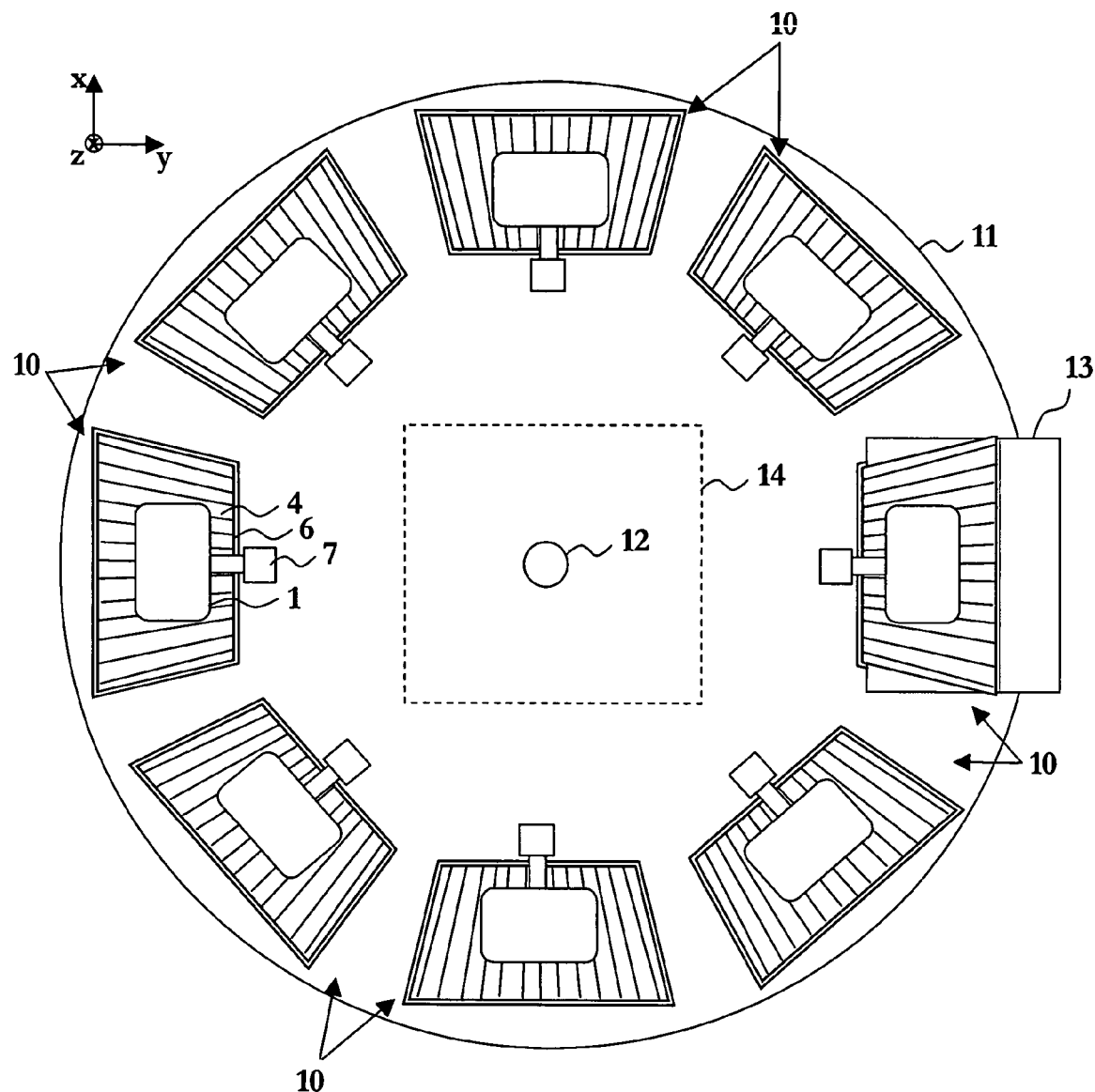

An arrangement for obtaining tomosynthesis data at high repetition rates for x-ray examination of an object according to an alternative preferred embodiment of the present invention is schematically illustrated in FIG. 4 in top view. This embodiment is identical with the embodiment of FIG. 3 except for that the line detectors 6a of each detector apparatus 10 are arranged 11 radially with respect to the axis 12 of rotation instead of being arranged parallel with each other within each detector apparatus 10. The reconstruction model has naturally to be modified to deal with the non-parallel arrangement of the line detectors 6a.

It shall be noted that the present invention is applicable to any kind of examination employing tomosynthesis or laminographic imaging, including e.g. mammography examination and other soft tissue examinations.

A preferred line detector for use in the present invention is a gaseous-based parallel plate detector, preferably provided with an electron avalanche amplifier. Such a gaseous-based parallel plate detector is an ionization detector, wherein electrons freed as a result of ionization by ionizing radiation are accelerated in a direction essentially perpendicular to the direction of the radiation.

For further details regarding such kind of gaseous-based line detectors for use in the present invention, reference is made to the following U.S. patents by Tom Francke et al. and assigned to XCounter AB of Sweden, which patents are hereby incorporated by reference: U.S. Pat. Nos. 6,546,070; 6,522,722; 6,518,578; 6,118,125; 6,373,065; 6,337,482; 6,385,282; 6,414,317; 6,476,397; and 6,477,223. It shall particularly be pointed out that such kind of detector is very efficient in preventing Compton scattered radiation from being detected. This property is of outermost importance to obtain high-quality tomosynthesis data.

The distance between the parallel plates, i.e. electrodes, of the line detector may be below about 2 mm, preferably below about 1 mm, more preferably below about 0.5 mm, and most preferably between about 0.1 mm and 0.5 mm. XCounter AB has recently begun to verify the Compton scattering rejection characteristics of the line detector experimentally and good contrast has been observed using a wide X-ray spectrum of high energy X-rays, at which conditions a conventional detector system would not be capable to see any structure at all. It is believed that the above-depicted gaseous-based line detector discriminates more than 99% of the scattered photons; and by proper design it is assumed that about 99.9% or more of the scattered photons can be prevented from being detected.

It shall, nevertheless, be realized that any other type of detector may be used in the present invention. Such line detectors include scintillator-based arrays, CCD arrays, TFT- and CMOS-based detectors, liquid detectors, and solid-state detectors such as one-dimensional PIN-diode arrays with edge-on, near edge-on or perpendicular incidence of X-rays, possibly with a collimator structure in front to partly reject scattered X-rays.

It shall further be noted that that the structure 7 for rigidly connecting the X-ray source 1, the collimator 4, and the radiation detector 6 may be exchanged for separate devices (not illustrated) for the X-ray source 1, the collimator 4 and the radiation detector 6, which may be controlled electronically to obtain synchronous linear movements of the separate devices to obtain the similar scanning movement.

It shall still further be noted that the radiation detector 6 of the apparatus of FIG. 1 may be modified such that the line detectors, instead of being arranged in a linear stack, are arranged at the periphery of a circle, the center of which coinciding with the position of radiation source 1.

Advantages of the present invention include:

A large number of consecutive images can be recorded during a short period of time. The number is set by the number of scanning-based detector apparatuses used and the rotational speed of the scanning movement.

The forces on the detector apparatuses, i.e. the radiation sources and the radiation detectors are small and constant in time. No mechanical vibrations will occur.

Only two X-ray tubes have to be switched on at a time, which means that each X-ray source can be cooled while except when it is required for the measurement, i.e. when it is right above the object table 13. Each X-ray tube has to be switched on only during about 1/N of the revolution time, where N is the number of scanning-based detector apparatuses used. As a consequence, a large number of consecutive images per second can be recorded without overheating the X-ray tubes.

Cheaper X-ray tubes can be used since it does not need to have a large heat capacity.

There are no limitations whatsoever regarding the width and length of the scanning-based detector apparatuses in the arrangement. The larger widths the scanning-based detector apparatuses have, the larger tomosynthesis angle is obtained. The length of each line detector may be limited. If a longer line detector is needed, several line detectors may be arranged side by side in order to together simulate one long line detector. Such arrangement is disclosed in the published U.S. Patent Application No. 20030155518 by Tom Francke, the contents of which being hereby incorporated by reference.

The dose to the patient is lower compared to CT.

The exposure time is short which means that any blurredness due to movement of or by the object is minimized.

By using the gaseous-based parallel plate detector, preferably provided with an electron avalanche amplifier described above a rather cheap arrangement can be provided, with radiation detectors which are direction sensitive, i.e. they have extremely low noise from scattered photons, and which have no electronic noise, i.e. they provide for photon counting with excellent signal-to-noise ration for individual photons.

The invention claimed is:

1. A scanning-based arrangement for obtaining tomosynthesis data of an object at high repetition rate comprising:
   a support structure having an axis of rotation;
   a plurality of scanning-based apparatuses fixedly arranged on said support structure at an essentially similar distance from said axis of rotation, each of said plurality of scanning-based apparatuses including:
      a divergent radiation source emitting radiation centered around an axis of symmetry; and
      a radiation detector comprising a stack of line detectors for creating tomosynthesis data, each line detector being directed towards the divergent radiation source to allow a ray bundle of said radiation that propagates in a respective one of a plurality of different angles to enter the line detector;
   an object table on which said object is arranged, said object table being arranged in the radiation path between the divergent radiation source and the radiation detector of one of said plurality of scanning-based apparatuses; and
   a device provided for rotating said support structure around said axis of rotation relative said object table so that said object table will successively be arranged in the radiation path between the divergent radiation source and the radiation detector of each of said plurality of scanning-based apparatuses, during which rotation each of the line detectors of each of said plurality of scanning-based apparatuses is adapted to record a plurality of line images of radiation as transmitted through said object in a respective one of said plurality of different angles, wherein said axis of rotation is substantially parallel with each of said axes of symmetry.

2. The arrangement of claim 1 wherein the number of said plurality of scanning-based apparatuses is between 2 and 20.

3. The arrangement of claim 1 wherein the number of said plurality of scanning-based apparatuses is between 2 and 10.

4. The arrangement of claim 1 wherein the number of said plurality of scanning-based apparatuses is between 4 and 8.

5. The arrangement of claim 1 wherein said plurality of scanning-based apparatuses is arranged equiangularly around said axis of rotation.

6. The arrangement of claim 1 wherein said essentially similar distance is between about 0.5 m and about 4 m.

7. The arrangement of claim 1 wherein said essentially similar distance is between about 0.5 m and about 2 m.

8. The arrangement of claim 1 wherein said essentially similar distance is about 1 m.

9. The arrangement of claim 1 wherein said support structure is an essentially circular disk.

10. The arrangement of claim 1 wherein said device provided for rotating is adapted to rotate said support structure relative said object table at a rotational speed of between about 0.2 revolutions per second and about 10 revolutions per second.

11. The arrangement of claim 1 wherein said device provided for rotating is adapted to rotate said support structure relative said object table at a rotational speed of between about 0.5 revolutions per second and about 5 revolutions per second.

12. The arrangement of claim 1 wherein said device provided for rotating is adapted to rotate said support structure relative said object table at a rotational speed of between about 0.5 revolutions per second and about 2 revolutions per second.

13. The arrangement of claim 1 wherein said plurality of different angles is distributed over an angular range of at least 5°.

14. The arrangement of claim 1 wherein said plurality of different angles is distributed over an angular range of at least 20°.

15. The arrangement of claim 1 wherein said plurality of different angles is distributed over an angular range of at least 45°.

16. The arrangement of claim 1 wherein the length of each of the line detectors in the stack of line detectors of each of said plurality of scanning-based apparatuses is between about 0.05 m and 2 m.

17. The arrangement of claim 1 wherein the length of each of the line detectors in the stack of line detectors of each of said plurality of scanning-based apparatuses is between about 0.1 m and 1 m.

18. The arrangement of claim 1 wherein the length of each of the line detectors in the stack of line detectors of each of said plurality of scanning-based apparatuses is between about 0.2 m and 0.5 m.

19. The arrangement of claim 1 wherein a width of the stack of line detectors of each of said plurality of scanning-based apparatuses is between about 0.2 m and 2 m.

20. The arrangement of claim 1 wherein a width of the stack of line detectors of each of said plurality of scanning-based apparatuses is between about 0.4 m and 1.5 m.

21. The arrangement of claim 1 wherein a width of the stack of line detectors of each of said plurality of scanning-based apparatuses is between about 0.75 m and 1.25 m.

22. The arrangement of claim 1 wherein the number of line detectors in the stack of line detectors of each of said plurality of scanning-based apparatuses is at least 2.

23. The arrangement of claim 1 wherein the number of line detectors in the stack of line detectors of each of said plurality of scanning-based apparatuses is at least 5.

24. The arrangement of claim 1 wherein the number of line detectors in the stack of line detectors of each of said plurality of scanning-based apparatuses is at least 10.

25. The arrangement of claim 1 wherein the number of line detectors in the stack of line detectors of each of said plurality of scanning-based apparatuses is between about 20 and about 50.

26. The arrangement of claim 1 wherein said device provided for rotating is adapted to rotate said support structure relative said object table an angle which is sufficient for scanning each of the line detectors of each of said scanning-based apparatuses across the entire object to obtain, for each of the line detectors of each of said scanning-based apparatuses, a two-dimensional image of radiation as transmitted through said object in a respective one of said plurality of different angles.

27. The arrangement of claim 1 wherein the line detectors of each of said plurality of scanning-based apparatuses are arranged parallel with each other.

28. The arrangement of claims 1 wherein each of the line detectors in the stack of line detectors of each of said plurality of scanning-based apparatuses is arranged radially with respect to said axis of rotation.

29. The arrangement of claim 1 wherein the divergent radiation source of each of said scanning-based apparatuses is an X-ray source; and the line detectors of each of said scanning-based apparatuses are each a gaseous-based ionization detector, wherein electrons freed as a result of ionization by a respective ray bundle are accelerated in a direction essentially perpendicular to the direction of that ray bundle.

30. The arrangement of claim 29 wherein said gaseous-based ionization detector is an electron avalanche detector.

31. The arrangement of claim 1 wherein the line detectors of each of said scanning-based apparatuses are each any of a diode array, a scintillator-based array, a CCD array, a TFT- or CMOS-based detector, or a liquid detector.

32. The arrangement of claim 1 wherein each of said scanning-based apparatuses comprises a collimator arranged in the radiation path immediately downstream of the radiation source of that scanning-based apparatus, said collimator preventing radiation, which is not directed towards the line detectors of that scanning-based apparatus, from impinging on said object, thereby reducing the radiation dose to said object.

33. A scanning-based method for obtaining tomosynthesis data of an object at high repetition rate using a scanning-based arrangement comprising a support structure having an axis of rotation; and a plurality of scanning-based apparatuses fixedly arranged on said support structure at an essentially similar distance from said axis of rotation, each of said plurality of scanning-based apparatuses including a divergent radiation source emitting radiation centered around an axis of symmetry, and a radiation detector comprising a stack of line detectors for creating tomosynthesis data, each line detector being directed towards the divergent radiation source to allow a ray bundle of said radiation that propagates in a respective one of a plurality of different angles to enter the line detector, said method comprising the steps of:

arranging said object in the radiation path between the divergent radiation source and the radiation detector of one of said plurality of scanning-based apparatuses; and rotating said support structure around said axis of rotation relative said object so that said object will successively be arranged in the radiation path between the divergent radiation source and the radiation detector of each of said plurality of scanning-based apparatuses, during which rotation, by means of each of said line detectors of each of said plurality of scanning-based apparatuses, a plurality of line images of radiation as transmitted through said object in a respective one of said plurality of different angles is recorded, wherein said axis of rotation is substantially parallel with each of said axes of symmetry.

34. The method of claim 33 wherein said support structure is rotated relative said object table at a rotational speed of between about 0.2 revolutions per second and about 10 revolutions per second.

35. The method of claim 33 wherein said support structure is rotated relative said object table at a rotational speed of between about 0.5 revolutions per second and about 5 revolutions per second.

36. The method of claim 33 wherein said support structure is rotated relative said object table at a rotational speed of between about 0.5 revolutions per second and about 2 revolutions per second.

37. The method of claim 33 wherein said support structure is rotated relative said object table an angle which is sufficient for scanning each of the line detectors of each of said scanning-based apparatuses across the entire object to obtain, for each of the line detectors of each of said scanning-based apparatuses, a two-dimensional image of radiation as transmitted through said object in a respective one of said plurality of different angles.

38. A scanning-based arrangement for obtaining tomosynthesis data of an object comprising:

a plurality of scanning-based apparatuses fixedly arranged relative each other at an essentially similar distance from an axis of rotation for said fixedly arranged plurality of scanning-based apparatuses, each of said fixedly arranged plurality of scanning-based apparatuses comprising a divergent radiation source emitting radiation centered around an axis of symmetry, and a stack of line detectors for creative tomosynthesis data, each of which being directed towards the divergent radiation source to allow a ray bundle of the radiation that propagates in a respective one of a plurality of different angles to enter the line detector and be detected therein;

an object region, in which said object is arranged, said object region being capable of being placed in the radiation paths between the divergent radiation sources and the stack of line detectors of said fixedly arranged plurality of scanning-based apparatuses; and a device for rotating said fixedly arranged plurality of scanning-based apparatuses around the axis of rotation relative said object region so that said object region will sequentially be in the radiation path between the divergent radiation source and the stack of line detectors of each of said fixedly mounted plurality of scanning-based apparatuses, while each of the line detectors of each of said plurality of scanning-based apparatuses is capable of recording a plurality of line images of radiation as transmitted through said object in a respective one of said plurality of different angles, wherein said axis of rotation is substantially parallel with each said axes of symmetry.

39. A method for obtaining tomosynthesis data of an object at using a plurality of scanning-based apparatuses arranged at an essentially similar distance from an axis of rotation for said plurality of scanning-based apparatuses, each of said plurality of scanning-based apparatuses comprising a radiation source emitting radiation centered around an axis of symmetry and a stack of line detectors, each of which being directed towards the radiation source to allow a ray bundle of radiation that propagates in a respective one of a plurality of different angles to enter the line detector to be detected therein, said method comprising the steps of:

placing said object in the radiation path between the radiation source and the stack of line detectors of one of said plurality of scanning-based apparatuses; and rotating said plurality of scanning-based apparatuses around said axis of rotation relative said object so that said object will sequentially be placed in the radiation path between the radiation source and the stack of line detectors of each of said plurality of scanning-based apparatuses, during which rotation, by means of each of said line detectors of each of said plurality of scanning-based apparatuses, a plurality of line images of radiation as transmitted through said object in a respective one of said plurality of different angles is recorded, wherein said axis of rotation is substantially parallel with each said axes of symmetry.

* * * * *